US008999241B2

(12) United States Patent
Katsumi et al.

(10) Patent No.: US 8,999,241 B2
(45) Date of Patent: Apr. 7, 2015

(54) SPECIMEN ANALYZER

(75) Inventors: Hironori Katsumi, Kobe (JP); Tsuyoshi Fukuzaki, Akashi (JP)

(73) Assignee: Sysmex Corporation, Kobe (JP)

(*) Notice: Subject to any disclaimer, the term of this patent is extended or adjusted under 35 U.S.C. 154(b) by 68 days.

(21) Appl. No.: 13/417,897

(22) Filed: Mar. 12, 2012

(65) Prior Publication Data

US 2012/0237398 A1 Sep. 20, 2012

(30) Foreign Application Priority Data

Mar. 16, 2011 (JP) ................................. 2011-058480
Mar. 16, 2011 (JP) ................................. 2011-058481

(51) Int. Cl.
*G01N 35/00* (2006.01)
*G01N 35/04* (2006.01)

(52) U.S. Cl.
CPC ........ *G01N 35/00* (2013.01); *G01N 2035/0443* (2013.01); *G01N 2035/0455* (2013.01); *G01N 2035/00435* (2013.01); *G01N 2035/00306* (2013.01)

(58) Field of Classification Search
CPC ............... G01N 2035/0443; G01N 2035/0455
See application file for complete search history.

(56) References Cited

U.S. PATENT DOCUMENTS

| 2005/0123445 | A1 | 6/2005 | Blecka et al. | |
|---|---|---|---|---|
| 2009/0004057 | A1 | 1/2009 | Sato | |
| 2010/0248346 | A1* | 9/2010 | Kaneko et al. | 435/287.1 |
| 2011/0223063 | A1* | 9/2011 | Katsumi et al. | 422/68.1 |

FOREIGN PATENT DOCUMENTS

| EP | 1102068 A1 * | 5/2001 |
|---|---|---|
| JP | 02-184345 * | 7/1990 |

* cited by examiner

*Primary Examiner* — P. Kathryn Wright
(74) *Attorney, Agent, or Firm* — Brinks Gilson & Lione

(57) ABSTRACT

A specimen analyzer comprising: a reagent refrigerator configured to store and cool a reagent container; a measurement unit configured to measure a specimen by using a reagent in the reagent container cooled by the reagent refrigerator; wherein the reagent refrigerator comprises: a housing configured so that an upper portion of the housing is openable and closable; a reagent container table configured so that the reagent container is set thereon, wherein the reagent container table is arranged within the housing so as to space away from a bottom of the housing; a first member arranged so as to face a side surface of the reagent container set on the reagent container table; and a second member arranged lower than the reagent container table, wherein the second member has a higher thermal conductivity than that of the first member.

17 Claims, 10 Drawing Sheets

SPECIMEN ANALYZER

RELATED APPLICATIONS

This application claims priority under 35 U.S.C. §119 to Japanese Patent Application Nos. 2011-058480 and 2011-058481 both filed on Mar. 16, 2011, the entire contents of which are hereby incorporated by reference.

BACKGROUND OF THE INVENTION

1. Field of the Invention

The present invention relates to a specimen analyzer for analyzing a sample using a cooled reagent.

2. Description of the Related Art

There are known specimen analyzers provided with a reagent refrigerator for cooling reagent within an accommodated reagent container, wherein the specimen analyzer analyzes specimens using the reagent cooled within a reagent refrigerator (for example, U.S. Patent Application Publication No. 2009/0004057). The reagent refrigerator disclosed in U.S. Patent Application Publication No. 2009/0004057 is configured to accommodate a reagent container within a reagent case that is cooled by Peltier element, and cool the reagent within the reagent container by circulating the air within the reagent case via a circulation unit, the reagent case being formed of a material that has excellent thermal conductivity, such as aluminum or the like.

The reagent refrigerator disclosed in U.S. Patent Application Publication No. 2009/0004057 readily generates condensation, particularly in the reagent case, because the reagent case has high thermal conductivity and is cooled by a Peltier element. Hence, when the user sets a reagent container in the reagent case, there is concern that the reagent container may come into contact with the side walls and the like of the reagent case causing condensation water to adhere to the reagent container. Condensation water adhering to the reagent container may interfere with the reading of the barcode label adhered to the reagent container, and there is further concern that condensation water may penetrate into the reagent container.

SUMMARY OF THE INVENTION

The scope of the present invention is defined solely by the appended claims, and is not affected to any degree by the statements within this summary.

According to a first aspect of the present invention, a specimen analyzer comprising: a reagent refrigerator configured to store and cool a reagent container; a measurement unit configured to measure a specimen by using a reagent in the reagent container cooled by the reagent refrigerator; wherein the reagent refrigerator comprises: a housing configured so that an upper portion of the housing is openable and closable; a reagent container table configured so that the reagent container is set thereon, wherein the reagent container table is arranged within the housing so as to space away from a bottom of the housing; a first member arranged so as to face a side surface of the reagent container set on the reagent container table; and a second member arranged lower than the reagent container table, wherein the second member has a higher thermal conductivity than that of the first member.

DETAILED DESCRIPTION OF THE PREFERRED EMBODIMENTS

Figure 1:
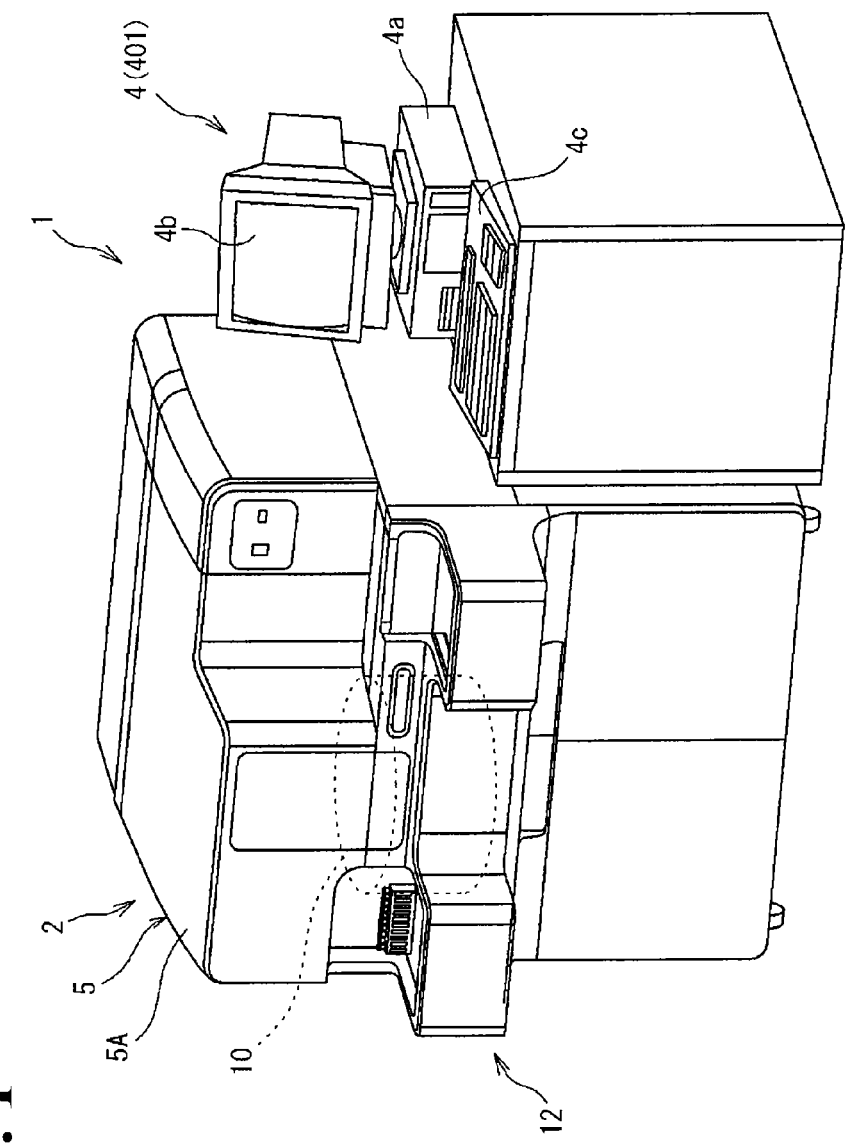
FIG. 1 is a perspective view showing the general structure of a specimen analyzer of an embodiment of the present invention.

The embodiments of the specimen analyzer of the present invention are described in detail hereinafter with reference to the accompanying drawings. FIG. 1 is a perspective view showing the general structure of a specimen analyzer 1 of an embodiment of the present invention.

The specimen analyzer 1 is an apparatus for performing specific measurements of a measurement sample prepared by mixing a reagent and a specimen collected from a human body, then analyzing the specimen based on the measurement results, and is, for example, a blood coagulation measuring apparatus, immunoanalyzer, or biochemical analyzer. The specimen analyzer 1 is configured by a measuring device 2, and a control device 4 that is electrically connected to the measuring device 2. Provided within a casing 5 of the measuring device 2 is a reagent refrigerator 10 for accommodating and cooling a plurality of reagent containers which hold reagent. The casing 5 of the measuring device 2 has a cover body 5A that can be opened and closed; at least part of the reagent refrigerator 10 can be exposed by opening the cover body 5A.

Figure 2:
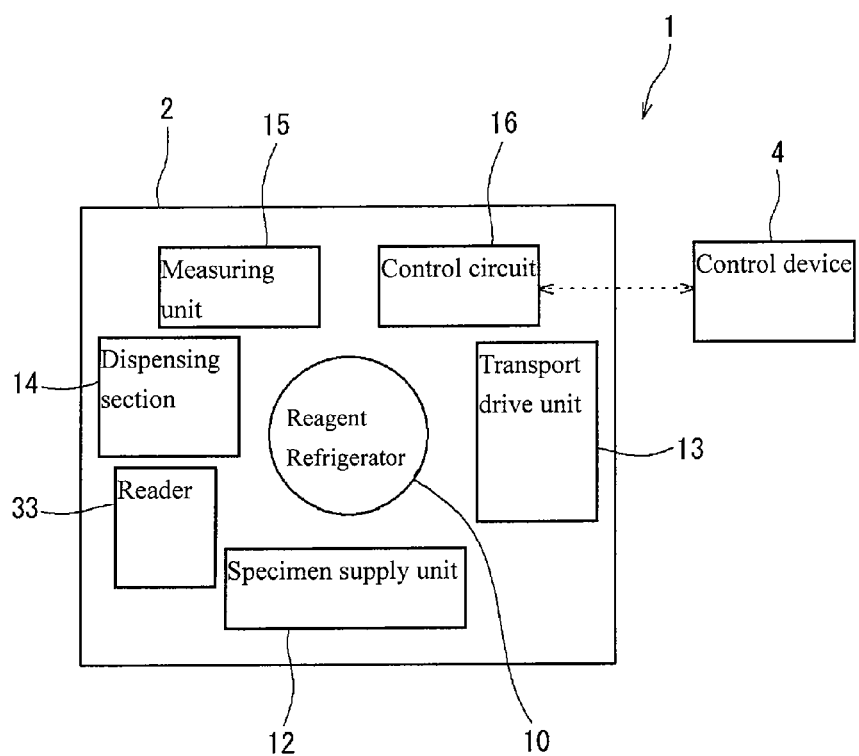
FIG. 2 is a brief structural view of the specimen analyzer of FIG. 1.

FIG. 2 is a brief structural view of the specimen analyzer 1 of FIG. 1. The measuring device 2 of the specimen analyzer 1 is provided with, in addition to the reagent refrigerator 10, a specimen supply unit 12, transport drive unit 13, dispensing section 14, measuring unit 15, reader 33, and control circuit 16. The specimen supply unit 12 has the function of setting a specimen rack that holds specimen containers (test tubes or the like) containing a specimen, and positioning each specimen container at a predetermined dispensing position by transporting the specimen rack. The transport drive unit 13 has the function of transporting the reagent container accommodated in the reagent refrigerator 10 to the predetermined dispensing position.

Figure 3:
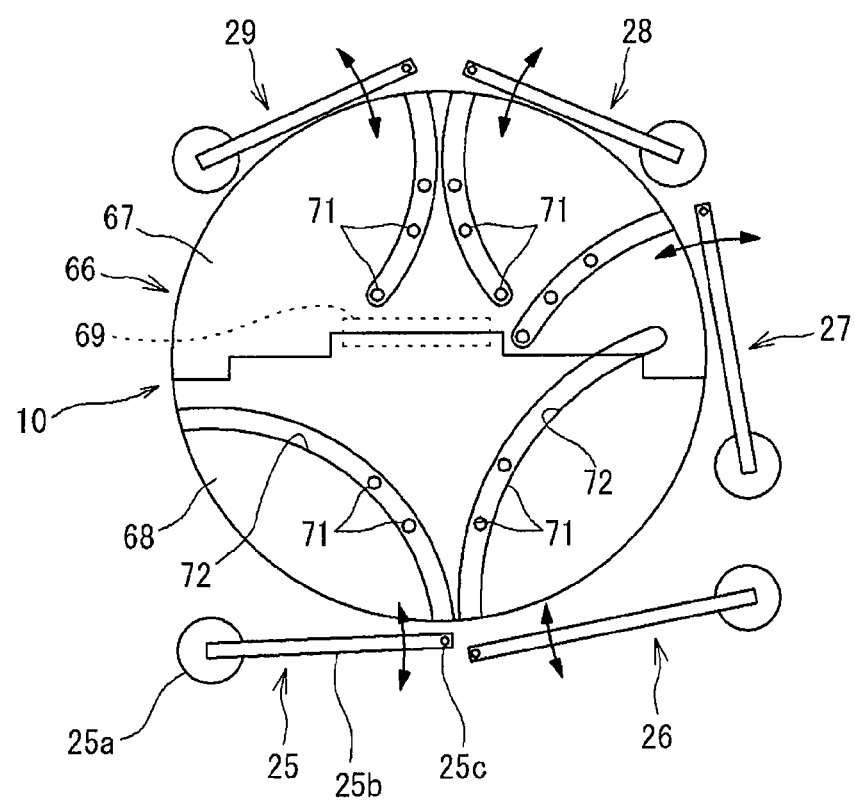
FIG. 3 is a brief plan view showing the reagent refrigerator and dispenser unit.

The dispensing section 14 has the function of dispensing specimen and reagent from the specimen container and reagent container positioned at the predetermined dispensing positions to prepare a measurement sample. FIG. 3 is a plan view showing the reagent refrigerator 10 and the dispensing section 14. As shown in FIG. 3, the dispensing section 14 has a plurality of dispensing units 25 through 29; each dispensing unit 25 through 29 is capable of dispensing reagent from within the reagent container accommodated in the reagent refrigerator 10.

When describing a single dispensing unit 25 by way of example, the dispensing unit 25 has a support 25a, an arm 25b wherein the base end is supported by the support 25a, and a pipette 25c provided at the tip of the arm 25b. The arm 25b is driven to pivot on the base end to rotate in horizontal directions and is further driven to ascend and descent in vertical directions. The pipette 25c is inserted into an aspiration hole 71 formed in the top surface of the reagent refrigerator 10, and aspirates reagent from the reagent container 300 (refer to FIG. 5) within the reagent refrigerator 10 via the horizontal rotation and vertical elevator action of the arm 25b. The other dispensing units 26 through 29 have structures identical to that of the dispensing unit 25, and their detailed description is therefore omitted.

Figure 5:
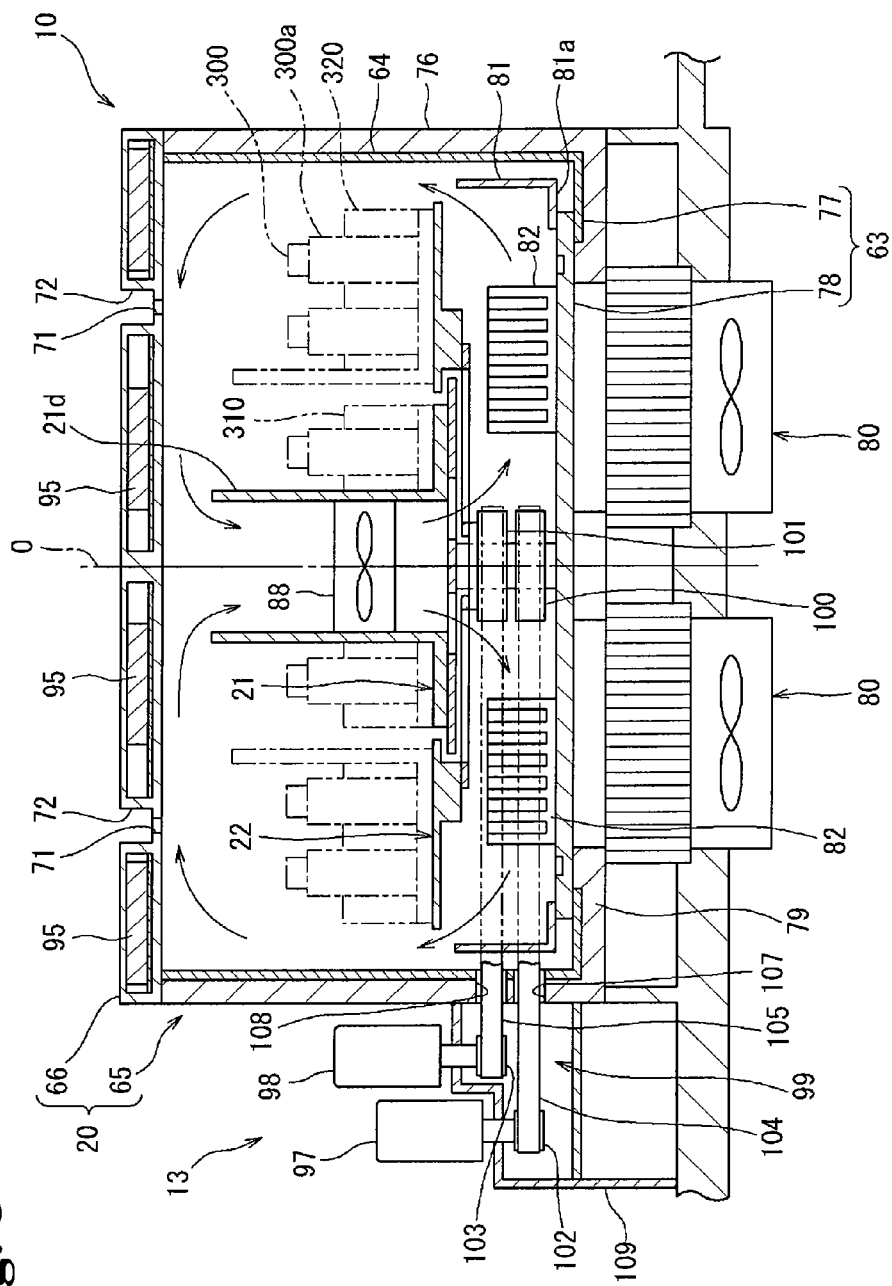
FIG. 5 is a side cross sectional view briefly showing the reagent refrigerator of FIG. 1.

As shown in FIG. 2, the measuring unit 15 has the function of performing specific measurements of the measurement sample prepared by mixing a specimen and reagent. The reader 33 is a barcode reader for reading a barcode adhered to the reagent container racks 310 and 320 (refer to FIG. 5) that accommodate the reagent container 300, and the reagent container 300 accommodated in the reagent refrigerator 10. As shown in FIG. 5, the reagent container 300 has a side surface 300a. The barcode is adhered to the side surface 300a. The reader 33 is disposed outside the reagent refrigerator 10, and is capable of reading a barcode within the reagent refrigerator 10 through a slit (not shown in the drawing) which is formed in the reagent refrigerator 10 and is opened and closed via a shutter.

As shown in FIG. 2, the control circuit 16 has a CPU, memory such as RAM, ROM or the like, and a communication interface; the control circuit 16 has the function of controlling the operations of the reagent refrigerator 10, transport drive unit 13, dispensing unit 14, measuring unit 15, and reader 33, and transmitting and receiving various types of information to/from the control device, to which the control circuit 16 is connected so as to be capable of communication.

As shown in FIG. 1, the control device 4 is a personal computer 401 (PC), and includes a controller 4a, display 4b, and keyboard 4c for inputting information. The controller 4a has the functions of transmitting an operation start signal of the measuring device 2 to the control circuit 16 of the measuring device 2, and analyzing the information of the measurement result obtained by the measuring device 2. The display 4b has the function of displaying the analysis result obtained by the controller 4a.

Detailed Structure of the Reagent Refrigerator 10

FIG. 5 is a side sectional view briefly showing the reagent refrigerator 10.

The reagent refrigerator 10 is provided to refrigerate the reagent container 300 containing a reagent to be added to a specimen, and transport the reagent container 300 in a rotational direction around an axis O. The reagent is prevented from degenerating by being preserved at low temperature. The reagent refrigerator 10 is provided with a housing 20, and reagent container tables 21 and 22 arranged within the housing 20 and loaded with reagent containers 300 containing reagent.

The reagent container tables 21 and 22 are configured by annular first reagent table 21, and an annular reagent container table 22 arranged concentrically with the first reagent container table 21 and on the outer side in the diameter direction of the first reagent container table 21. The first reagent container table 21 and the second reagent container table 22 are arranged so that the first reagent container rack 310 and the second reagent container rack 320 holding a plurality of reagent containers 300 are respectively detachable.

The first reagent container table 21 and the second reagent container table 22 are respectively and independently rotatable in both clockwise and counterclockwise directions on the axis O via the transport drive unit 13. Hence, the reagent containers 300 set on the reagent container tables 21 and 22 are transported in rotational directions. Each reagent container 300 is positioned at the dispensing position of the dispensing units 25 through 29 by transporting the reagent container 300 in a rotational direction. Details of the structure of the transport drive unit 13 are described later.

As shown in FIG. 5, the reagent refrigerator 10 and the housing 20 are provided with a solid-bottom cylindrical shaped main body 65 with a bottom wall 63 forming the bottom part of the housing 20 and a circumferential wall (side wall) 64 rising from the periphery of a bottom wall 63, and a cover 66 that functions as a top wall of the reagent refrigerator 10 by closing the top opening of the main body 65. The sealed space circumscribed by the main body 65 and the cover 66 is a refrigeration chamber, and the plurality of reagent containers 300 set in the reagent container tables 21 and 22 within the refrigeration chamber are enclosed completely therein on the outside in the diameter direction (outside in the horizontal direction) by the circumferential wall 64.

As shown in FIG. 3, the cover 66 is configured by a fixed cover 67 that closes approximately the back half of the main body 65, and a movable cover 68 that closes the approximate front half of the main body 65 and is openable. The movable cover 68 is coupled to the front edge of the fixed cover 67 so as to oscillate through a hinge member 69.

The cover 66 of the housing 20 has a plurality of aspiration holes 71 formed therein; these aspiration holes 71 are configured so that the pipette 25c of the dispensing units 25 through 29 can be inserted, and the reagent within the reagent container 300 held in the reagent refrigerator 10 can be aspirated from the top opening of the reagent container 300.

Figure 4:
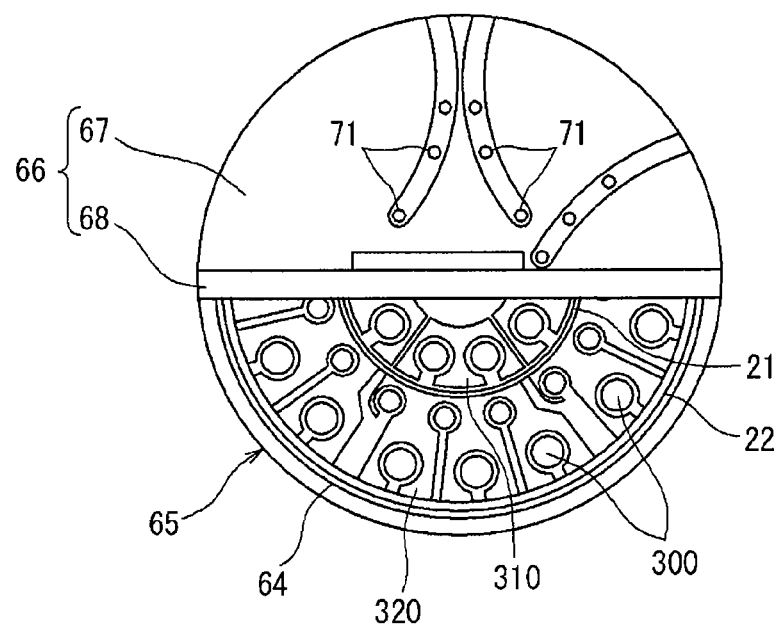
FIG. 4 is a brief plan view showing top surface of the housing in an opened condition.

Note that exchanging the reagent in the reagent refrigerator 10 is accomplished for each reagent container rack 310 and 320 by opening the cover 5A (refer to FIG. 1) of the measuring device 2 to expose the front side of the reagent refrigerator 10, opening the movable cover 68 upward to open the front half of the reagent refrigerator 10. FIG. 4 is a plan view of the reagent refrigerator showing the cover 66 in the open condition. When the cover 66 is open, the interior of the main body 65 is exposed, and the reagent racks 310 and 320 holding the reagent containers 300 can be inserted into the main body 65 and removed from the main body 65.

As shown in FIG. 5, the circumferential wall (side wall) 64 of the main body 65 of the housing 20 is formed of a material having low thermal conductivity. The bottom wall 63 has different material for the outer part 77 and the heat transfer layer 78; the outer part 77 is formed of the same low thermal conductivity material as the circumferential wall 64 and is linked to the bottom end of the circumferential wall 64.

The heat transfer layer 78 of the bottom wall 63 is formed of a material that has a higher thermal conductivity than the circumferential wall 64 and the outer part 77, and protrudes upward from the outer part 77. The circumferential wall 64, bottom wall 63, and outer part 77 of the main body 65 may be formed of thermoplastic resin such as ABS and the like. The heat transfer layer 78 may be formed of a metal such as aluminum, iron, steel and the like. The outer surface of the circumferential wall 64 and the bottom wall 63 are covered by thermal shield layers 76 and 79 that have lower thermal conductivity.

Figure 6:
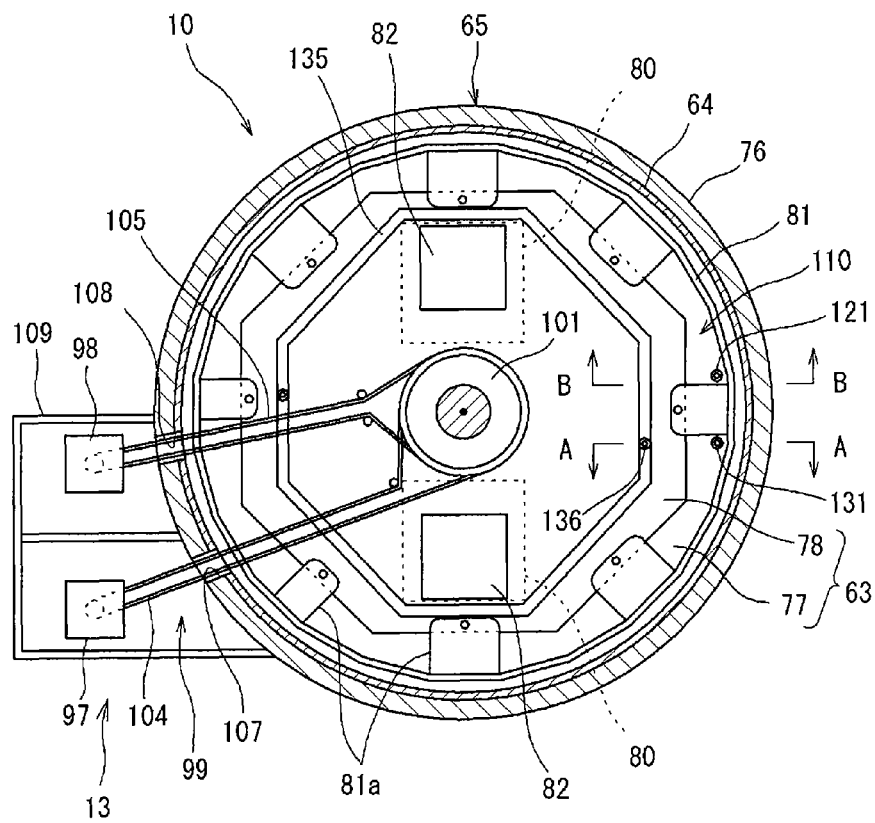
FIG. 6 is a horizontal cross sectional view of the inner bottom surface of the reagent refrigerator viewed from above.

FIG. 6 is a horizontal cross sectional view of the inner bottom surface of the reagent refrigerator 10 viewed from above. As shown in FIG. 6, the heat transfer layer 78 provided on the bottom wall 63 of the housing 20 is formed in a polygonal shape (hexagonal shape in the example of the drawing) in the plan view. As shown in FIGS. 5 and 6, part of the bottom surface of the heat transfer layer 78 is exposed below, and a cooler 80 is provided on this exposed surface. In the present embodiment, two coolers 80 are arranged at symmetrical positions centered on the central axis O of the reagent refrigerator 10 (that is, the center of rotation of the first and second reagent container tables 21 and 22). The cooler 80 is configured to cool the air within the reagent refrigerator 10 using the heat transfer layer 78 as a cooling medium by directly cooling the heat transfer layer 78 which has a high thermal conductivity. Note that the cooler 80 is not limited to using a Peltier element, and also may provide cooling, for example, by air cooling or water cooling the heat transfer layer 78. The planar shape of the heat transfer layer 78 is not limited a polygonal shape, and also may be circular.

An upright wall member 81 is provided in the circumferential direction along the circumferential wall 64 on the inside of the circumferential wall 64 of the main body 65. As shown in FIG. 5, the upright wall member 81 is positioned below the top surface of the first and second reagent container tables 21 and 22, and is separated from the inner surface of the circumferential wall 64 at the inner side of the circumferential wall 64. As shown in FIG. 6, the upright wall member 81 is formed with an approximately circular shape in the plan view, and extends the approximate entire circumference of the housing 20. Note that the upright wall member 81 of the present embodiment has an approximately circular shape by curving a band-like plate in a polygonal shape.

A mounting part 81a that protrudes inward in the diameter direction is provided at the bottom end of the upright wall member 81, and the upright wall member 81 is connected to the heat transfer layer 78 by the mounting part 81a being screwed to the top surface of the heat transfer layer 78. The upright wall member 81 is formed of metal, for example, aluminum, that is a material that has the same high thermal conductivity as the heat transfer layer 78. The upright wall member 81 connected to the heat transfer layer 78 and is cooled by the cooler 80.

A heat sink (condensation promoting member) 82 is provided on the top surface of the heat transfer layer 78. The heat sink 82 is formed of a material having a high thermal conductivity such as aluminum, and increases the surface area by having a plurality of protuberances or fins. As shown in FIG. 6, the heat sinks 82 are respectively provided positions above the two coolers 80, and are cooled by the coolers 80 through the heat transfer layer 78. Note that the heat transfer layer 78, upright wall member 81, and heat sink 82 configure the "second member" in the present embodiment.

As shown in FIG. 5, in the reagent refrigerator 10, a cylindrical ventilation body 21d stands in the center of the first reagent container table 21, and a forced air fan (fan unit) 88 is provided within the ventilation body 21d. The forced air fan 88 is configured to blow the air taken in from above the ventilation body 21d downward in the ventilation body 21d, the ventilation body 21d being the air flow pass. The airflow produced by the forced air fan 88 therefore blows on the heat transfer layer 78 that is directly cooled by the cooler 80. The airflow is thus effectively cooled.

The airflow produced by the forced air fan 88 flows outward in the radial direction after striking the heat transfer layer 78, and changes direction upward after striking the upright wall member 81, so that the air flows between the circumferential wall 64 (inside surface) of the reagent refrigerator 10 and the second reagent container table 22 and upward above the second reagent container table 22. Thereafter, the air flows in an inward radial direction along the bottom surface of the cover 66, and is taken into the top of the forced air body 21d so as to be once again blown downward by the forced air fan 88, hence, circulating the air within the reagent refrigerator 10. The reagent in the reagent container 300 placed in the first and second reagent container tables 21 and 22 is cooled to a desired temperature, for example, approximately 10° C., by the air circulated by the forced air fan 88.

Condensation is facilitated by the heat transfer layer 78, upright wall member 81, and heat sink 82 because the high thermal conductivity heat transfer layer 78, upright wall member 81, and heat sink 82 are exposed in the region below the top surfaces of the first and second reagent container tables 21 and 22 and the heat transfer layer 78, upright wall member 81, and heat sink 82 are cooled by the coolers 80. On the other hand, condensation is inhibited mainly because the low thermal conductivity circumferential wall 64 (first member in the present invention) is arranged in the region above the top surfaces of the first and second reagent container tables 21 and 22.

Accordingly, condensation is produced solely below the top surface of the first and second reagent container tables 21 and 22 and condensation is inhibited above the top surface of the first and second reagent container tables 21 and 22 even though warm outside air flows into the housing 20 when the movable cover 68 of the cover 66 is opened and a reagent container 30 is set inside the housing 20. Therefore, condensation water is prevented from adhering to the reagent container 300 even when the reagent container 300 comes into contact with the circumferential wall 64 while being set within the housing 20. The problem of condensation water adhering to the reagent container 300 and, for example, the problems of condensation water penetrating into the reagent container 300 and adversely affecting the reading of the barcode adhered on the reagent container 300 are likewise avoided.

The circumferential wall 64 is directly cooled by the upright wall member 81 which is cooled by the cooler 80 since the upright wall member 81 is arranged a distance from the inner surface of the circumferential wall 64 on the inner side of the circumferential wall 64 of the housing 20. The circumferential wall 64 is therefore not overly cooled, and the formation of condensation on the circumferential wall 64 is inhibited.

Figure 8:
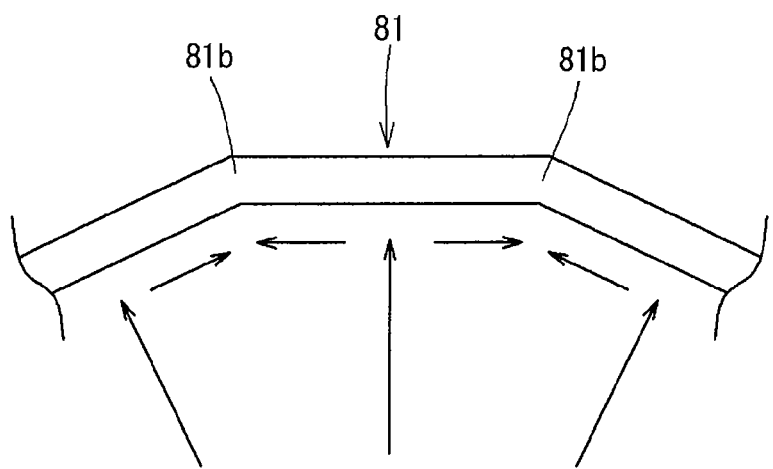
FIG. 8 is a plan view showing part of the upright wall member.

The upright wall member 81 is formed in a polygonal shape in plan view. As shown in FIG. 8, the airflow at the inner surface of the upright wall member 81 is directed toward a corner angle 81b of the upright wall member 81, which changes the direction upward. Hence, the upright wall member 81 functions to direct the flow of the air upward. The air is effectively cooled since the airflow is within the entire inner surface of the upright wall member 81, which is cooled by the cooler 80.

A cover heater 95 (refer to FIG. 5) is provided inside the cover 66, and the cover 66 is warmed by the cover heater 95. Specifically, as shown in FIGS. 3 and 5, a channel 72, which extends along the movement track of the arm 25b of the dispensing units 25 through 29, is formed in the top surface of the cover 66, and an aspirating hole 71 is formed in the channel 72. The cover 66 becomes thin in the part of the channel 72, and is therefore easily cooled by the cool air in the housing 20 so that external air readily condenses. Condensation formation is prevented in the channel 72 and penetration of condensation water into the housing 20 from the aspirating hole 71 is prevented by providing the cover heater 95 inside the cover 66 in the region of the channel 72.

As shown in FIG. 5, the first and second reagent container tables 21 and 22 are driven in rotation by the transport drive unit 13. Specifically, the transport drive unit 13 has a first drive body 97 and a second drive body 98 configured by stepper motors or the like. The first and second drive bodies 97 and 98 are arranged at the side of the housing 20, and are connected to the first and second reagent container tables 21 and 22 through a power transmission device 99. The power transmission device 99 is configured by a first driven pulley 100, second driven pulley 101, first drive pulley 102, second drive pulley 103, first transmission belt 104, and second transmission belt 105. The first driven pulley 100 and the second driven pulley 101 are arranged on the center axis O of the reagent refrigerator 10, and are supported by the bottom part of the housing 20 so as to be relatively mutually rotatable. The first reagent container table 21 is connected to the first driven pulley 100, and the second reagent container table 22 is connected to the second driven pulley 101.

The first driven pulley 102 is mounted on the output shaft of the first drive body 97, and the second drive pulley 103 is mounted on the output shaft of the second drive body 98. The first drive belt 104 is reeved around the first driven pulley 100 and the first drive pulley 102, and the second drive belt 105 is reeved around the second driven pulley 101 and the second drive pulley 103. Therefore, the first reagent container table 21 can be rotated through the first drive pulley 102, first transmission belt 104, and first driven pulley 100 by operating the first drive body 97; the second reagent container table 22 can be rotated through the second drive pulley 103, first transmission belt 105, and second driven pulley 101 by operating the second drive body 98.

A first insertion opening 107 and a second insertion opening 108 are formed in the circumferential wall 64 of the housing 20 for the first drive transmission belt 104 and the second drive transmission belt 105 to pass through. At the side of the reagent refrigerator 10 is formed a chamber 109 to maintain airtightness and that is circumscribed by a heat insulating material; the receptacle 109 is connected to the reagent refrigerator 10 through the first insertion opening 107 and the second insertion opening 108. Part of the drive shafts of the first and second drive bodies 97 and 98, and the first and second drive pulleys 102 and 103, the first and second transmission belts 104 and 105 are arranged in the chamber 109. Therefore, since cool air is prevented within the chamber 109 even though the cool air within the housing 20 leaks from the first and second insertion openings 107 and 108, there is no reduction in the cooling efficiency within the housing 20.

Since the first drive body 97 and the second drive body 98 are arranged at the side of the reagent refrigerator 10, condensation does not adhere to the first drive body 97 and the second drive body 98 even when condensation water formed within the reagent refrigerator 10 spreads downward from the reagent refrigerator 10, hence damage to the first drive body 97 and the second drive body 98 is prevented.

Note that the first drive body 97 and the second drive body 98 are not limited to the side of the reagent refrigerator 10, and may be arranged anywhere, even outside the reagent refrigerator 10, with the exclusion of below the reagent refrigerator 10. Although the power transmission device 99 is a transmission device employing drive belts reeved on pulleys, the present invention is not limited to this arrangement inasmuch as other drive transmission device also may be used, such as a gear transmission device.

Figure 7:
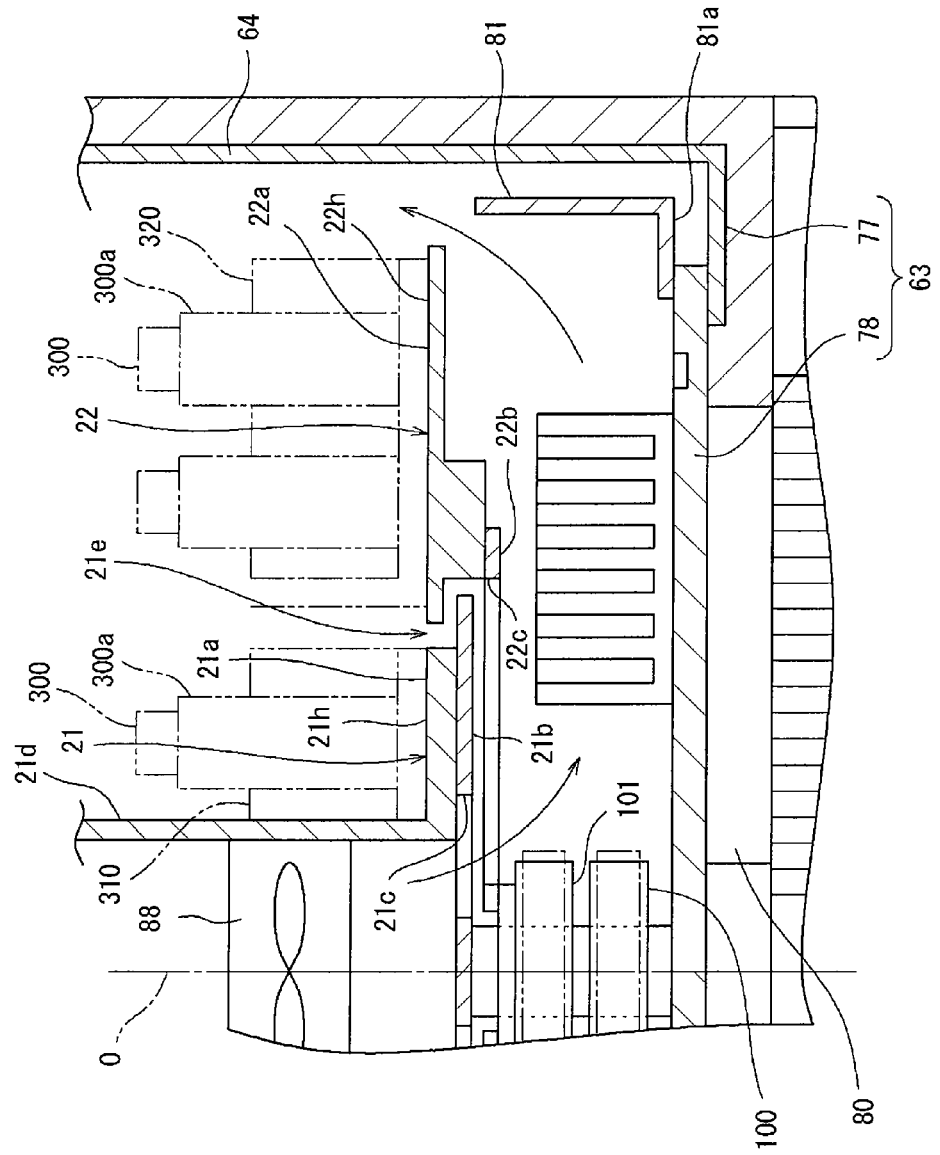
FIG. 7 is a side cross sectional view briefly showing the enlarged essential parts within the reagent refrigerator.

FIG. 7 is a side cross sectional view briefly showing the enlarged essential parts within the reagent refrigerator 10.

Figure 10:
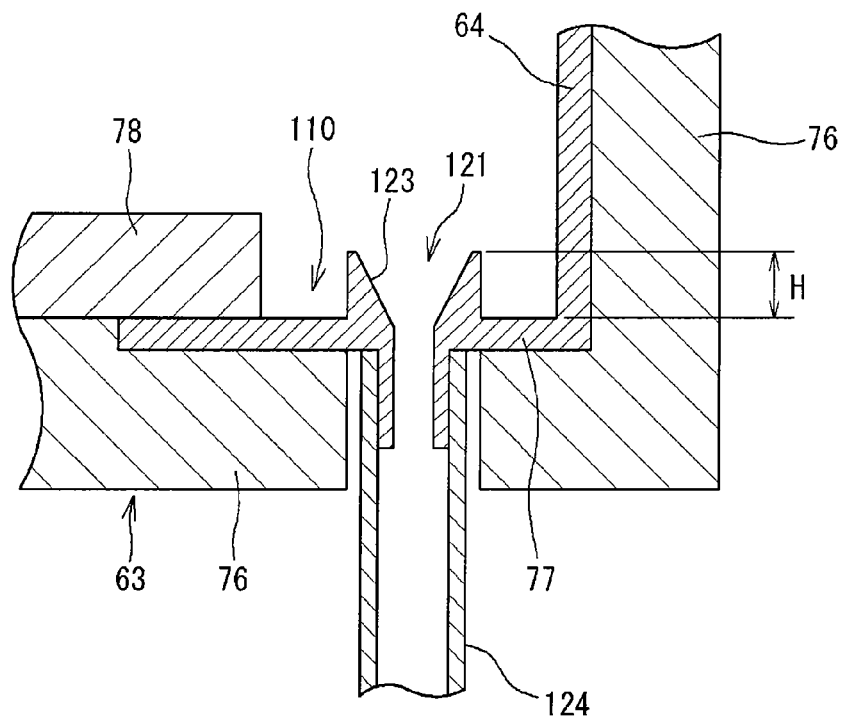
FIG. 10 is a cross sectional view on the B-B arrow line in FIG. 6.

As shown in FIG. 10, the first reagent container table 21 has a first placement part 21a with a top surface 21h for setting a reagent container 300, and a first support part 21b for supporting the first placement part 21a from the bottom side; the center part of the first support part 21b is connected to the first driven pulley 100 so as to be integratedly rotatable. A plurality of first openings 21c are formed with spacing in the circumferential direction from the center (region below the forced air fan 88) of the first support part 21b, and air flows vertically through the first openings 21c. The outer circumference end of the first support part 21b is positioned outside in the radial direction from the outer circumference end of the first placement part 21a, and a concave step part 21e is formed in an approximate L-shape at the top surface side of the circumferential edge of the first reagent container table 21.

The second reagent container table 22 has a second placement part 22a with a top surface 22h for setting a reagent container 300, and a second support part 22b for supporting the second placement part 22a from the bottom side; the center part of the second support part 22b is connected to the second driven pulley 101 so as to be integratedly rotatable. A plurality of second openings 22c are formed with spacing in the circumferential direction of the second support part 22b, and air flows vertically through the second openings 22c.

Note that in the present embodiment, the first placement part 21a of the first reagent container table 21 is made of synthetic resin such as ABS or the like, and the second placement part 22a of the second reagent container table 22 is made of metal such as aluminum or the like. Alternatively, the first placement part 21a of the first reagent container table 21 may be made of metal, and the second placement part 22a of the second reagent container table 22 may be made of synthetic resin, or both may be made of synthetic resin or of metal. From the perspective of inhibiting formation of condensation, the placement parts 21a and 22a of the first and second reagent container tables 21 and 22 are most suitably both made of low conductivity synthetic resin.

The outer peripheral edge of the first reagent container table 21, that is, the outer circumferential edge of the first support part 22b, is arranged to be outside in the radial direction from the inner peripheral edge of the second reagent container table 22, that is, the inner circumferential edge of the second placement part 22a. Thus, the outer peripheral edge of the first reagent container table 21 and the inner peripheral edge of the second reagent container table 22 overlap in a vertical direction so that no space occurs between the tables 21 and 22 in the plan view. The dimension of the overlap of the tables 21 and 22 is designated t.

The outer peripheral edge of the first reagent container table 21 is arranged on the bottom side of the inner peripheral edge of the second reagent container table 22. That is, when the airflow direction C below the first and second reagent container tables 21 and 22 is set as standard, the outer peripheral edge of the first reagent container table 21 positioned upstream of the airflow direction C is disposed below the inner peripheral edge of the second reagent container table 22 positioned on the downstream side. Therefore, the air flowing below the first and second reagent container tables 21 and 22 is unlikely to escape upward through the gap of the first and second reagent container tables 21 and 22. Below the first and second reagent container tables 21 and 22, an airflow can be reliably produced from the center of the housing 20 to the circumferential wall 64 of the housing 20, thus suitably producing circulating air within the housing 20.

The inner peripheral edge of the second reagent container table 22 is arranged to fit into the step part 21e of the first reagent container table 21, so that the top surface of the first reagent container table 21 and the top surface of the second reagent container table 22 are mutually at the same height. Thus, the heights of the reagent containers 300 of both reagent container tables 21 and 22 are the same, and the elevator strokes of the pipette 25c in the dispensing units 25 through 29 (refer to FIG. 3) are uniform when aspirating reagent from the reagent container 300. Operational control of the dispensing units 25 through 29 is therefore simplified. Moreover, there is no contact between the outer peripheral edge of the first reagent container table 21 and the inner peripheral edge of the second reagent container table 22, and both tables 21 and 22 can rotate smoothly with little rotational friction even without a gap between the tables 21 and 22 in the plan view.

As shown in FIG. 6, an annular first circumferential channel 135 is formed in the outer circumferential side of the heat transfer layer 78 provided on the bottom wall 63 of the housing 20. The first circumferential channel 135 has the function of collecting condensation water formed by the heat transfer layer 78. The first circumferential channel 135 is polygonal in shape (hexagonal in the example of the drawing) in plan view similar to the heat transfer layer 78. A first drain hole 136 is formed in the bottom surface of the first circumferential channel 135.

Figure 9:
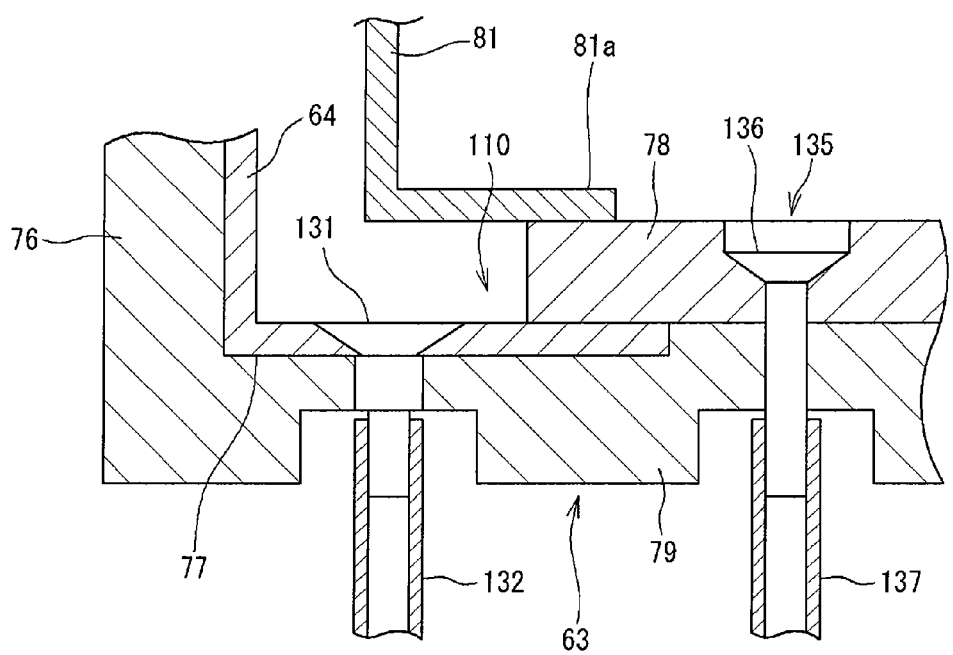
FIG. 9 is a cross sectional view on the A-A arrow line in FIG. 6.

FIG. 9 is a cross sectional view on the A-A arrow line in FIG. 6. The first drain hole 136 is connected to a first drain pipe 137. The condensation water collected in the first circumferential channel 135 is discharged from the first drain hole 136 by periodically operating a pump (not shown in the drawing) that is connected to the first drain pipe 137.

As shown in FIG. 6, since the heat transfer layer 78 provided on the bottom wall 63 of the reagent refrigerator 10 is formed higher than the outer peripheral part in the outside radial direction, a second circumferential channel 110 is formed in the bottom surface of the outer circumferential part 77 between the heat transfer layer 78 and the circumferential wall 64. The second circumferential channel 110 is positioned below the upright wall member 81. Accordingly, the condensation water formed on the upright wall member 81 and the condensation water formed on the outer circumferential part of the heat transfer layer 78 is mainly collected in the second circumferential channel 110.

A second drain hole 121 and a third drain hole 131 are formed in the second circumferential channel 110. As shown in FIG. 9, the third drain hole 131 is formed flush with the bottom surface (top surface of the outer circumferential part 77) of the second circumferential channel 110, and a third drain pipe 132 is connected to the third drain hole 131. The condensation water collected in the second circumferential channel 110 is discharge from the third drain hole 131 by periodically operating a pump (not shown in the drawing) connected to the third drain pipe 132.

FIG. 10 is a cross sectional view on the B-B arrow line in FIG. 6. A cylindrical preventer 123 is formed on the circumferential edge of the second drain hole 121, and protrudes upward from the bottom surface of the second circumferential channel 110. The preventer 123 has an apex height H that is lower than the top surface of the heat transfer layer 78. The second drain hole 121 is connected to a third drain pipe 124. When an amount of condensation water is collected in the second circumferential channel 110 that exceeds the preventer 123, the condensation water overflows the preventer 123 and is naturally discharged from the second drain hole 121 to the outside.

The present invention is not limited to the above embodiment and may be variously modified insofar as such modifications are within the scope of the claims.

For example, although the forced air fan 88 generates an airflow that flows from top to bottom, an airflow also may be generated that flows from bottom to top. The flow of the air below the first and second reagent container tables 21 and 22 also may flow inward in the radial direction toward the center axis O of the circumferential wall 64 of the housing 20.

The upright wall member 81 also may be provided so as to contact the inner surface of the circumferential wall 64 of the housing 20, and also may be detached from the heat transfer layer 78. The upright wall member 81 also may be inclined so that the top part is positioned at the outside in the radial direction, thereby increasing the effect of changing the direction of the airflow.

Although the first member of the present invention is configured by the circumferential wall 64 of the housing 20 of the reagent refrigerator 10 in the above embodiment, the first member may be configured by a low thermal conductivity member that is separate from the circumferential wall 64, for example, a member arranged along the inner side of the circumferential wall 64. In this case, the circumferential wall 64 may be formed of a high thermal conductivity material such as metal. It is preferable that the first member is configured by the circumferential wall 64 of the housing 20 as in the above embodiment because the first member reduces the space for placement of the reagent container 300 within the housing 20 when the first member is configured by a member that is separate from the circumferential wall 64.

The first member and the second member of the present invention are not limited to provision extending the entirety of the housing 20, inasmuch as the first and second members also may be provided at intervals or provided intermittently. Particularly the first member also may be provided in a part allowing easy touching of the reagent container 300 when setting the reagent container 300 in the housing 20. For example, as shown in FIG. 4, only the part of the circumferential wall 64 of the housing 200 that is exposed when the movable cover 68 of the cover 66 is opened may be formed of low thermal conductivity material, while the other parts (parts normally hidden by the cover 66) are formed of high thermal conductivity material.

The first member and the second member of the present invention also may both be configured by the circumferential wall 64. In this case, the part of the circumferential wall 64 above the top surface of the first and second reagent container tables 21 and 22 may be formed by a low thermally conductive material, and the part below the top surface of the first and second reagent container tables 21 and 22 may be formed of high thermally conductive material.

The transport drive unit also may relatively rotate both reagent container tables 21 and 22 by rotating one or another of the first reagent container table 21 and the second reagent container table 22.

What is claimed is:
1. A specimen analyzer comprising:
   a measurement unit configured to measure a specimen by using a reagent in the reagent container;
   a reagent refrigerator configured to store and cool a reagent container, the reagent refrigerator comprising:
   a housing configured so that an upper portion of the housing is openable and closable;
   a reagent container table configured so that the reagent container is set thereon, wherein the reagent container table is within the housing so as to be spaced away from a bottom of the housing;
   a first member arranged so as to face a side surface of the reagent container, the first member comprising a material that is a part of a side wall of the housing above the reagent container table; and
   a second member lower than the reagent container table, wherein the second member comprises a material that has a higher thermal conductivity than that of the mate- rial of the first member, the second member comprising heat transfer layer configuring the bottom of the housing and an upright wall member extending parallel to an inner surface of the side wall of the housing and along an inner periphery of the inner surface, the upright wall member spaced apart and separate from the side wall of the housing.

2. The specimen analyzer of claim 1, wherein the first member extends along an outer periphery of the reagent container table.

3. The specimen analyzer of claim 1, wherein the reagent refrigerator includes a cooling unit that cools the air within the housing and the cooling unit contacts at least a part of the second member.

4. The specimen analyzer of claim 3, wherein the reagent refrigerator includes a fan unit that circulates the air within the housing.

5. The specimen analyzer of claim 4, wherein the fan unit moves the air downward from above the reagent container table and at least part of the second member is shaped to direct the air supplied from the fan unit upward from below the reagent container table.

6. The specimen analyzer of claim 1, wherein the heat transfer layer is connected to the upright wall member.

7. The specimen analyzer of claim 1, wherein at least a part of the reagent container table comprises a member that has a lower thermal conductivity than the second member.

8. The specimen analyzer of claim 1, wherein the material of first member comprises a synthetic resin and the material of second member comprises a metal.

9. The specimen analyzer of claim 1, further comprising:
a channel that collects condensation water adhered to the second member; and
a water discharge device that discharges the water collected in the channel.

10. The specimen analyzer of claim 9, wherein the channel is in a bottom surface of the second member and the water discharge device is in the channel.

11. The specimen analyzer of claim 1, further comprising a drive unit that drives the rotation of the reagent container table, wherein the drive unit is outside the housing in a region other than below the housing.

12. The specimen analyzer of claim 11, further comprising a power transmission unit, a part of which extends through the housing, to transmit power from the drive unit to the reagent container table; and
a chamber that preserves airtightness of a space within the housing, and accommodating at least one part of the power transmission unit and a part of the drive unit connected to part of the power transmission unit.

13. The specimen analyzer of claim 1, wherein the reagent container table comprises:
a first reagent table with an outer peripheral edge part opening a space above the bottom part of the housing within the housing;
an annular second reagent container table with an inner peripheral edge part on an outer periphery of the first reagent container table and opening a space above the bottom of the housing within the housing,
wherein the specimen analyzer comprises:
a drive unit that drives relative rotations of the first reagent container table and the second reagent container table;
a cooling unit that cools the air within the housing; and
a fan unit the circulates the air within the housing,
wherein the outer peripheral edge part of the first reagent container table and the inner peripheral edge part of the second reagent container table are arranged so as to overlap in a vertical direction.

14. The specimen analyzer of claim 13, wherein the first reagent container table and the second reagent container table are such that a top surface of the reagent container of the first reagent container table and a top surface of the reagent container of the second reagent container table are at identical heights.

15. The specimen analyzer of claim 13, wherein the first reagent container table and the second reagent container table are not in mutual contact.

16. The specimen analyzer of claim 13, wherein with respect to a direction of airflow below the first reagent container table and the second reagent container table, an edge part of one of the reagent container tables on an upstream side with respect to the direction of airflow is lower than an edge part of the other reagent container table on a downstream side with respect to the direction of airflow.

17. The specimen analyzer of claim 1, wherein a space between the upright wall member and the side wall of the housing is smaller than a space between an outer periphery edge part of the reagent container table and the side wall of the housing.

* * * * *

UNITED STATES PATENT AND TRADEMARK OFFICE
CERTIFICATE OF CORRECTION

| | | |
|---|---|---|
| PATENT NO. | : 8,999,241 B2 | Page 1 of 1 |
| APPLICATION NO. | : 13/417897 | |
| DATED | : April 7, 2015 | |
| INVENTOR(S) | : Hironori Katsumi et al. | |

It is certified that error appears in the above-identified patent and that said Letters Patent is hereby corrected as shown below:

In the Claims

In column 11, claim 1, line 1, after "member comprising" insert --a--.

In column 12, claim 13, line 19, after "a fan unit" replace "the" with --that--.

Signed and Sealed this
Fifth Day of January, 2016

Michelle K. Lee
*Director of the United States Patent and Trademark Office*